United States Patent [19]

Characklis

[11] Patent Number: 5,051,359

[45] Date of Patent: Sep. 24, 1991

[54] METHOD OF DETERMINING THE QUALITY OF A MEDIUM

[75] Inventor: William G. Characklis, Bozeman, Mont.

[73] Assignee: Research and Development Institution, Inc. at Montana State University, Bozeman, Mont.

[21] Appl. No.: 201,993

[22] Filed: Jun. 3, 1988

[51] Int. Cl.$^5$ .............................................. C12Q 1/18
[52] U.S. Cl. ........................................ 435/32; 435/29; 435/31; 435/805
[58] Field of Search ............................. 435/29, 31, 32

[56] References Cited

U.S. PATENT DOCUMENTS

| 2,708,178 | 5/1955 | Gyorgy | 435/29 |
| 3,684,702 | 8/1972 | Hartmann | 435/29 |
| 4,514,495 | 4/1985 | Schalkowsky | 435/29 |
| 4,517,292 | 5/1985 | Schalkowsky | 435/32 |
| 4,643,968 | 2/1987 | Weaver | 435/32 |

FOREIGN PATENT DOCUMENTS 0075215 3/1983 European Pat. Off. .

OTHER PUBLICATIONS

Microbiology Textbook, Davis et al., 1990, pp. 51–53.

*Primary Examiner*—Sam Rosen
*Attorney, Agent, or Firm*—Lowe, Price, LeBlanc & Becker

[57] ABSTRACT

An in situ method of determining the quality of a medium capable of supporting cellular growth comprises obtaining viable cells which are anchored to a substrate, determining the value of at least one characteristic of the cell which is proportional by a factor to the number of the cells present under conditions which preserve cell viability, calculating the number of cells present by multiplying the value of the characteristic by the factor, exposing the cells to the medium by in situ immersing the substrate with the anchored cells in the medium for a period of time and under conditions which preserve the viability of the cells and permit cell growth, withdrawing the cells from the medium, repeating the steps for determining the value of the characteristic of the cells and for calculating the number of cells present, calculating the cell growth rate or the variation in the number of anchored cells per unit of time during the period of time from the formula cell variation/t=(N−N$_o$)/t and comparing the cell growth rate or the variation in the value obtained with a data base of average cell variation per unit time for the same cells in the same medium, wherein the quality of the fluid is below a minimum acceptable if the value is obtained is higher than a predetermined fraction of the corresponding data base value. An in situ method of determining the effectiveness of a biocide on the indigenous cell population of a medium comprises determining the quality of the medium by the above method, and if the quality of the medium is below the minimum acceptable, adding thereto an amount of biocide for a period of time effective to adjust the cell growth rate or the variation in the number of anchored cells per unit time to a predetermined value, and repeating the two previous steps as necessary until the quality of the medium is about at least equal to the minimum acceptable.

15 Claims, No Drawings

METHOD OF DETERMINING THE QUALITY OF A MEDIUM

TECHNICAL FIELD

This invention relates to a non-invasive method for determining the quality of an environment or medium capable of supporting cellular growth by measuring characteristics of viable cells anchored to a substrate before and after exposure of the cells in the environment for a period of time. This invention also relates to a method of determining the effectiveness of biocidal treatment on the indigenous cell population of an environment or medium by determining the quality of the medium by the method of the invention and if the quality is below a minimum acceptable adding a biocide to reduce the number of indigenous cells to a predetermined value.

BACKGROUND ART

The determination of the increase or decrease of an indigenous cell population in media, such as fluids or air, present in the ambient environment entails great difficulties for a variety of reasons. Amongst them that it is difficult, and sometimes impossible, to distinguish between the numerous species present in the ambient environment. This makes the design of a specifically tailored method for testing the presence of the cells extremely difficult.

Furthermore, many of the systems of interest such as water and oil reservoirs and gaseous environments are continuous flow systems In such systems it is extremely difficult to account for increases and decreases in cell numbers due to the inherent characteristics of the medium.

Moreover, in other instances the organisms grow in the medium in an anchored state, e.g., in the form of a biofilm. Repeated attachment and detachment of the organisms or cells in fact confounds the determination of cell counts or other properties in the biofilm.

In copending U.S. application Ser. No. 201,994 filed June 3, 1988 now U.S. Pat. No. 4,912,332 by Characklis et al, entitled "NON-DESTRUCTIVE METHODS FOR DETECTING ORGANIC DEPOSITS AND REMOVING THEM", a non-destructive method for the in situ detection of organic materials, including cells, which deposit on the internal surface of a conduit through which a fluid flows was described. The detection is undertaken by means of light absorption spectrometry such as infrared (IR) spectroscopy or ultraviolet (UV) spectroscopy.

Therefore, a need still exists for a method of determining the quality of a liquid capable of supporting cellular growth by means of an exogenous cell population which can be placed in contact with the medium in situ for a desired period of time whereas the measurements of the variables are conducted away from the site.

DISCLOSURE OF THE INVENTION

This invention relates to a method of determining the quality of a medium capable of supporting cellular growth, comprising (a) obtaining viable cells which are anchored to a substratum;

(b) determining the value of at least one parameter associated with the anchored cells which is proportional by a factor to the number of cells present under conditions which preserve cell viability;

(c) calculating the number of cells $N_{(n-1)}$, wherein $n=1$, present by multiplying the cell parameter value by the factor;

(d) exposing the anchored cells to the medium for a period of time and under conditions which preserve the viability of the cells and permit cell growth;

(e) withdrawing the anchored cells from the medium;

(f) conducting steps (b) and (c) at a time $t_n$, wherein n is $n+1$;

(g) calculating the cell variation per unit of time $t_n$ from the formula cell variation$/t = (N_n - N_o)/t_n$; and (h) comparing the % cell variation per unit time with a data base comprising average % cell variations per unit time for the immobilized cells, wherein the quality of the medium is below a minimum acceptable if the value obtaining is higher than a predetermined fraction of the corresponding data base value.

The calculation of the cell variation/t of step (g) results in a cellular growth rate. If divided by the number of cells present, the specific growth rate can be determined as an artisan would know.

This invention also relates to a method of determining the effectiveness of a biocide on the indigenous cell population of a medium, comprising (I) determining the quality of the liquid by the method of the invention described above;

(II) if the quality of the medium is below the minimum acceptable, adding thereto an amount of biocide for a period of time effective to decrease the % cell variation per unit time to a predetermined value; and (III) repeating steps (I) and (II) until the quality of the liquid is at least about equal to the minimum acceptable.

Other objects, advantages and features of the present will become apparent to those skilled in the art from the following discussion.

BEST MODE FOR CARRYING OUT THE INVENTION

The present invention fulfills a long felt need for a method for testing the quality of media found in the environment which remedies the drawbacks described above in a simultaneously simple and versatile manner since for all practical purposes it may be applied to all contemplated media in the environment which are capable of sustaining cell growth.

In accordance with one aspect of the present invention a method is provided for the determination of the quality of a liquid which can support cellular growth. The method of determining the quality of a medium provided herein comprises (a) obtaining viable cells which are anchored to a substratum;

(b) determining the value of at least one parameter associated with the anchored cells which is proportional by a factor to the number of cells present under conditions which preserve cell viability;

(c) calculating the number of cells $N_{(n-1)}$, present by multiplying the cell parameter value by the factor;

(d) exposing the cells to the medium for a period of time and under conditions which preserve the viability of the cells and permit cell growth;

(e) withdrawing the cells from the medium;

(f) conducting steps (b) and (c) at a time $t_n$, wherein n is n+1;

(g) calculating the cell variation per unit of time $t_n$ from the formula $$\text{cell variation}/t = (N_n - N_o)/t_n; \text{ and}$$

(h) comparing the cell variation per unit time with a data base comprising average cell variations per unit time for the cells in the medium, wherein the quality of the medium is below a minimum acceptable if the value obtaining is higher than a predetermined fraction of the corresponding data base value.

The method relies on the utilization of viable cells which are anchored to a substratum. The substratum with the cells is exposed to the medium for a period of time capable of supporting a detectable growth of the cell population and at least one characteristic of the cells is measured prior to and subsequent to the substrate being exposed to the medium.

The value obtained for the characteristic tested prior to exposing the cells to the medium is then subtracted from the value obtained for the same characteristic after the cells are withdrawn from the liquid and divided by the time elapsed while the cells where immersed in the fluid in accordance with the following formula:

$$\text{cell variation}/t = (N_n - N_o)/t_n$$

Finally, the thus determined value for the cell variation per unit time is compared with a corresponding value from a database containing average values for cell; variations per unit time in the medium.

The method may be repeated in order to obtain several readings and average values and a standard deviation can be calculated by methods known in the art. However, as a first approximation a single value for the cell variation per unit time may be sufficient in order to qualitatively asses whether the fluid's condition is above or below average for supporting cell growth.

For instance, the quality of the liquid can be said to be below a minimum acceptable if the value for the cell variation per unit time obtained by practicing the method of the invention is higher than a predetermined fraction of the corresponding database value. Vice versa, if the value obtained for the cell variation per unit time by practicing the method of the invention is smaller than the corresponding database value multiplied by a predetermined factor it can be said that the quality of the fluid is above the minimum acceptable.

A person with ordinary skill in the art can determine without undue experimentation what these factors may be for particular media, media masses, flow rates and the like. By means of example, if the fluid is drinking water, a person in a water purification station will have access to data reflecting accepted operative parameters in terms of specific cell populations which can be specifically tailored for use with the methods of this invention.

For practicing the above method of the invention the cells are anchored to a substrate in a manner such that they cannot become easily unattached. In accordance with the present invention any composite material is suitable which comprises particulate biologically viable cells and also includes a support material to provide, inter alia, dimensional stability to the cells attached thereto.

In principle, any type of cells which can be attached to a substrate or embedded therein can be utilized as the exogenous cells for practicing this invention. By means of example, cells suitable for use with the method described herein are microorganisms such as bacteria, yeast and the like, plant cells, such a vinca plant cells and the like, and animal cells such a tissue culture cells. The cells must remain viable once attached to the substrate and be capable of growing in the medium whose quality is to be tested. The cells may be wild type or mutant cells, genetically engineered cells, or otherwise laboratory-made cells.

The cells may be attached to substrata. Examples are coupons, sheets, strips, plugs, microspheres such a glass microspheres, slides such a glass or metal slides, gels, dipsticks, or tho cells may be encapsulated and the like. The substrate itself may act as the support material for the cells or a support material may be added. The support material is to provided dimensional stability to the composite material and can be made of any suitable two- or three-dimensionally stable material capable of retaining the cells once they are attached to the substrate. Examples of two-dimensionally stable materials are nylon or steel mesh or other woven materials, porous particles, refined metal plates and ceramic surfaces, polymeric layers such as those formed with various types of celluloses, organic polymers and the like. Once the cells are attached to the substrate, a cover may be provided for the active material composition on the substrate material. The cover may be in the form of a permeable membrane and the like.

A variety of gel compositions for entrapping cells are known in the art and can be utilized as a substrate with this invention, particularly with the aid of a cover and/or a porous substrate, both of which were described above (see, U.S. Pat. Nos. 4,526,867 and 4,452,892, the entire contents of which are incorporated herein by reference).

Examples of encapsulating materials for the cells can be found in U.S. Pat. No. 4,663,286, the entire content of which is incorporated herein by reference.

Other support materials include conventional materials used for distillation and catalyst support reactions such as pellets, stars, spiral rings, cross partition rings, irregular spheroids, and the like. Other support materials can be metals, ceramics including both porcelain and stoneware clay ceramics including pottery clays, plastics including polyethylene, polypropylene and nylon, glass, woods such as redwood, stones, cement and cement aggregates, among others (e.g., U.S. Pat. No. 4,287,305, the entire content of which is incorporated herein by reference).

The cells may be immobilized on the substrate by a variety of methods known in the art (e.g., U.S. Pat. Nos. 4,578,351, 4,659,655, 4,287,305, 4,663,286, 4,452,892, and 4,526,867, the entire contents of which are incorporated herein by reference).

Good results are obtained when the cells are immobilized before the point in the growth cycle where any substantial senescence occurs. Such cells tend to have a longer useful life-time or in other terms they remain viable for a longer period of time than those cells that are immobilized later in the growth cycle. The best results are obtained when cells are immobilized in the logarithmic to mid-logarithmic phase of their growth cycle.

Subsequent to being immobilized the cells may be maintained in near-zero growth conditions (e.g., by use of an environment lacking growth hormones) or they may be used shortly after preparation. By way of example, the cells may be immobilized by applying an active material composition having selected rheological properties to a substrate and providing a cover for the active material composition (containing the cells) on the support material. When the cells are immobilized with the aid of a gel it must be ensured that the characteristics of the gel are such that if the diffusion of a substrate to the cell membrane is required for the tests, such diffusion will occur giving the characteristics of the gel.

It is to be understood that the composite material comprising the cells and the substrate may optionally be treated after formation and prior or subsequent to exposure to a medium to conditions such as freezing, refrigeration and the like. This is particularly useful for storage and/or transport purposes since the testing may be conducted at a site different from the testing site. In this manner the characteristics of the cells at the time the tests are made are preserved while the measurements may be taken at a later time.

The cells are typically distributed throughout the surface of a substratum or within a gel at a density such that will permit the growth of the cell population while at the same time allow the detection of variations in the values of specific characteristics of the cells which are to be measured. An artisan will be able to determine specific densities for the preparation of the composite materials without undue experimentation. In addition, a variety of composite substrates are available commercially which can also be utilized for the practice of this invention.

A large number of characteristics of the cells can be utilized for the measurements of the change in the cell population before and after exposure to the medium. Although not an exhaustive list, examples of these characteristics are provided hereinbelow. Changes in the weight of the composite substrate, calorimetric analysis by, for example, using a substrate which is converted to a detectable product by the cells (or vice versa) a detectable substrate that is converted to a non-detectable product, measurements of the turbidity or light absorption associated with the cells, and the like.

The methods for taking the measurements of the characteristics described above are known in the art and need not be described herein.

Steps (d) through (h) of the method of the invention discussed above may be repeated at preset intervals of time, e.g., over a prolonged period of time. Repeated measurements may be taken using the same composite substrate if the cells remain viable or with the aid of a new substrate. In the latter case, then the measurement corresponding to $N_o$ which is taken before the composite substrate is exposed to the medium must be taken for the new substrate. However, if various composite substrates are prepared with the same type of cells and having the same density of cells deposited thereon, the $N_o$ measurement need not be retaken every time a new composite substrate is utilized.

In a particular embodiment of the method of the invention the cells which are anchored to the substrate may comprise at least two different types of cells. When more than one type of cells are utilized, the different types of cells must be compatible with one another. That is, each type of cell must be capable of growing in the presence of the other cell type.

In a particularly preferred embodiment of the method of the invention the cells utilized comprise cells having growth rates similar to those cells which are indigenous to the medium. In this case the cell variation per unit time obtained in step (g) of the method can be taken as the measure of the growth rate of the indigenous cells in the medium.

In yet another particularly preferred embodiment of the method of the invention, the cells comprise cells of the same strain as the indigenous cells whose growth rate is desired to be determined.

The method of the invention may suitably be applied to a medium whose quality is to be determined which flows in a continuous or semi-continuous manner or to a medium which is stationary. In addition, the method of the invention may be applied in situ, or step (d) may be conducted on a sample of the medium withdrawn from the general medium mass.

The methods described herein my be applied to any medium capable of supporting the growth of cells, as long as cells capable of growing therein are utilized. Examples are water or aqueous solutions, milk and wine storage masses, oil wells, and the like.

This invention also provides a method of determining the effectiveness of a biocidal treatment on the indigenous cell population of a medium which comprises determining the quality of the medium by the method described above, and adding to the medium an amount of biocide for a period of time effective to decrease the cell variation per unit time to a predetermined value if the quality of the medium is below a minimum acceptable, and repeating the two previous steps until the quality of the liquid of the medium is at least about equal to the minimum acceptable, or to a preset value.

In the context of this invention a biocide is understood to be a chemical or other means of removing or inactivating biological materials such as cells, which are present in a medium. When cells from microbial or higher organisms are to be removed, the biocide may be a chemical such as chlorine, an antibiotic or other chemical compound which is lethal to the cells.

This method may be conducted under the conditions specified hereinabove in accordance to this invention.

The cell population, in other words, may consist of a single species or a mixed culture, and may be obtained by isolation from the indigenous environment or by growing a specific cell culture or mixed culture considered suitable for its similar characteristics to those of the indigenous cell population.

The methods of the invention may be suitably utilized to test for the effectiveness of bacterial inhibitors such a poisons in cooling water, ground water, injection water such as in oil fields, production water such as in oil fields, waste water and processed water. The methods of the invention are also suitable for testing mammalian systems such as bacterial infections, dental caries, food processing fluids and the like.

The methods of the invention can also be utilized for determining the in situ growth rates of indigenous bacteria in drinking water, waste water, industrial waters, foods, cooling water, ground water, injection water and production water such as those in oil fields, bacterial infections in animals, dental caries, food processing and the like.

These methods can also be utilized for testing the enrichment of a particular microbial species over others found in a mixed culture of a natural population by immobilizing such mixed culture on a substrate and then practicing the method of determining the quality of a medium of the invention by immersing the composite substrate in a solution having a specific substrate which can provide an energy source for the cells.

Having now generally described this invention, the same will be better understood by reference to the following example, which is included herein for purposes of illustration only and is not intending to be limiting of the invention or any other embodiment thereof, unless so specified.

EXAMPLE

A desired microbial species is isolated from the environment. Either a single species or a mixed cell population can be utilized. The cells are mixed with sodium alginate in an appropriate concentration to yield a desired cell concentration. The sodium alginate containing the cells is applied to a coupon and then contacted with calcium chloride. The liquid film becomes gelled on the coupon entrapping the immobilized cells. The number of cells on the coupon are determined by counting techniques or image analysis as is known in the art.

The coupon(s) are then inserted into a test environment and exposed thereto for an appropriate period of time. To determine the growth rate of the cells, the coupons are removed after a desired exposure time and the increase in the number of cells is determined as above and divided by the exposure time to determine the growth rate.

To determine biocide effectiveness the coupons are removed after a biocidal treatment and the number of viable cells is determined by methods known in the art or by adding nutrients to the coupons and observing the number of cells which form colonies, e.g., by means of an image analyzer.

The invention now being fully described, it will be apparent to one of ordinary skill in the art that many changes and modifications can be made thereto without departing from the spirit or scope of the invention as set forth herein.

I claim:

1. An in situ method of determining the quality of a medium capable of supporting cellular growth, comprising
   (a) obtaining viable cells which are anchored to a substrate;
   (c) determining the value of at least one parameter associated with the cells which is proportional by a factor to the number of cells present under conditions which preserve cell viability; p1 (d) calculating the number of cells $N_{(n-1)}$, wherein n=1, present by multiplying the cells' parameter value by the factor;
   (d) exposing the cells to the medium by in situ immersing the substrate with the anchored cells in the medium for a period of time and under conditions effective to preserve the viability of the cells and permit cell growth;
   (e) withdrawing the substrate with the anchored cells from the medium;
   (f) conducting steps (b) and (c) at a time $t_n$, wherein n is n+1;
   (g) calculating the cell growth rate or the variation in the number of anchored cells per unit time, $t_n$, from the formula cell variation/$t = (N_n - N_0)/t_n$; and (h) comparing the cell growth rate or the variation in the number of anchored cells per unit time with a data base comprising average cell variations per unit time for the cells in the medium, wherein the quality of the medium is below a minimum acceptable if the value obtained is higher than a predetermined fraction of the corresponding data base value.

2. The method of claim 1, wherein
   steps (d) through (h) are repeated at preset intervals of time.

3. The method of claim 1, wherein
   the cells are selected from the group consisting of animal and plant cells and microorganisms.

4. The method of claim 3, wherein
   the cells are a microorganism selected from the group consisting of bacteria and yeast.

5. The method of claim 3, wherein
   the cells are mammalian cells.

6. The method of claim 3, wherein
   the cells are plant cells.

7. The method of claim 3, wherein
   the cells comprise laboratory-made cells selected from the group consisting of mutated cells and recombinant cells.

8. The method of claim 1, wherein
   the cells comprise at least two different types of cells, wherein each type of cell is capable of growing in the presence of the other type.

9. The method of claim 1, wherein
   the substrate to which the cells are anchored is selected from the group consisting of a sheet, a plug, a gel, a dipstick, a microsphere, and a strip.

10. The method of claim 1, wherein
    the characteristic whose value is determined in step (b) is selected from the group consisting of weight, color development in the presence of a diffusible substrate, turbidity and light absorption.

11. The method of claim 1, wherein
    the cells utilized in step (a) comprise cells which are selected from the group consisting of cells having growth rates similar to cells indigenous to the medium; and
    the cell growth rate or the variation in the number of anchored cells per unit time obtained in step (g) is taken as a measure of the growth rate of the indigenous cells.

12. The method of claim 11, wherein
    the cells comprise cells of the same strain as the indigenous cells.

13. The method of claim 1, wherein
    the medium whose quality is being determined flows in a continuous or semi-continuous manner.

14. The method of claim 1, wherein
    the medium whose quality is being determined is selected from the group consisting of water, aqueous solutions, liquid foods and waste fluids.

15. An in situ method of determining the effectiveness of a biocide on the indigenous cell population of a medium, comprising
    (I) determining the quality of the medium by the method of claim 1;
    (II) if the quality of the medium is below the minimum acceptable, adding thereto an amount of biocide for a period of time effective to adjust the cell growth rate or the variation in the number of anchored cells per unit time to a predetermined value; and
    (III) repeating steps (I) and (II) until the quality of the medium is at least about equal to the minimum acceptable.

* * * * *